United States Patent [19]
de Medicis et al.

[11] Patent Number: 6,114,306
[45] Date of Patent: Sep. 5, 2000

[54] CYTOKINE RELATED TO HEMOLYTIC ANEMIA AND METHOD OF USE

[75] Inventors: Eveline de Medicis, Sherbrooke; Andre Larochelle, Toronto, both of Canada

[73] Assignee: Universite de Sherbrooke, Quebec, Canada

[21] Appl. No.: 08/834,224

[22] Filed: Apr. 15, 1997

Related U.S. Application Data

[63] Continuation-in-part of application No. 08/546,872, Oct. 23, 1995.

[51] Int. Cl.[7] .......................... A61K 38/19; C12N 15/19; C07K 14/475; C07K 14/52
[52] U.S. Cl. ................ 514/12; 514/2; 435/355; 435/372; 435/377; 424/533; 530/350; 530/351; 530/380
[58] Field of Search ..................... 514/2, 12; 530/350, 530/380, 351; 424/533; 435/355, 372, 377

*Primary Examiner*—Lorraine Spector
*Assistant Examiner*—Claire M. Kaufman
*Attorney, Agent, or Firm*—Nixon & Vanderhye P.C.

[57] ABSTRACT

Pyruvate kinase deficiency is a blood disease characterized by hemolytic anemia. PCR analysis of cDNA leukocytic extracts of patients with hereditary pyruvate kinase deficiency anemia revealed two overexpressed markers when compared to extracts from healthy individuals. These two markers, proposed as human markers A and B and associated with hereditary hemolytic anemia, have been cloned (HUMDNAMA and HUMDNAMB, Gen Bank Association numbers M64700 and M64701). Our attention has focused on human DNA marker B, a 451 bp open-reading frame. The marker has been cloned in the bacteria vector pGEX-2TK and the expressed protein, called HMF (hemolytic anemia related factor), has been tested for biological activity. It has been observed that the HMF-glutathione transferase fusion protein, added to freshly prepared leukocytes cultures, has an immediate cytotoxic effect and a delayed lymphoblastic effect. The lymphoblastic effect is greatly enhanced when erythrocytes are added to the leucocytes. The sequence of HUMDNAMB is 48% homologous to bovine interferon A-alpha, and 63% in the region 303–416 bp. The matrix analysis of the amino acid sequence of HMF reveals also a structural similarly with interferon. Structural properties and biological activities of HMF support a its role as a cytokine.

8 Claims, 9 Drawing Sheets

FIG_4

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear    (xi) SEQUENCE DESCRIPTION: SEQ ID NO:1:

AGCCCAGAGG GACTGGTGAC C      21

(2) INFORMATION FOR SEQ ID NO:2:

(i) SEQUENCE CHARACTERISTICS:
      (A) LENGTH: 22 base pairs
      (B) TYPE: nucleic acid
      (C) STRANDEDNESS: single
      (D) TOPOLOGY: linear    (xi) SEQUENCE DESCRIPTION: SEQ ID NO:2:

CTTCACGCCT TCGTGGTTCT CA      22

(2) INFORMATION FOR SEQ ID NO:3:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:3:

GGTCACCAGT CCCTCTGGGC T                                                      21

(2) INFORMATION FOR SEQ ID NO:4:

(i) SEQUENCE CHARACTERISTICS:
        (A) LENGTH: 149 amino acids
        (B) TYPE: amino acid
        (C) STRANDEDNESS: single
        (D) TOPOLOGY: linear (xi) SEQUENCE DESCRIPTION: SEQ ID NO:4:

Pro Arg Gly Thr Gly Asp Pro Ser Pro Gly Leu Gly Gly Cys Gln Glu
    1               5                   10                  15

Gly Ser Cys Gly Gly Ala Ser Val Gly Leu His Ser Gly Arg Asp Arg
                20                  25                  30

His Pro Ser Gly Trp Ser Arg Ser Gly His Cys Pro Glu Ala Leu Arg
            35                  40                  45

Glu Gly Ala Ala Ala Ala Ser Pro Ala Glu Ala Cys Arg Leu Ser
    50                  55                  60

Ser Pro Gly Thr Ala Val Met Pro Ser His Ser Glu Glu Lys Gly Arg
    65                  70                  75                  80

Glu Ser Ala Leu Leu Leu Ser Ala Ala Glu Met Gly Cys His Leu Pro
                85                  90                  95

Leu Gly Leu Val Ala Leu Gln Lys Glu Gly Gln Gly Ala Pro Gly Ser
                    100                 105                 110

Gly Ser Arg His Pro Arg Glu Ala Gln Ala Asp Leu Gln Gly Gln Pro
                115                 120                 125

Cys Pro Gly Ala Gly Gly Cys Ser Ala Pro Gly Cys Val Ser Val Val
                130                 135                 140

Thr Ser Pro Ser Gly
    145

(2) INFORMATION FOR SEQ ID NO:5:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (xi) SEQUENCE DESCRIPTION: SEQ ID NO:5:

AGCCCAGAGG GACTGGTGAC CCTTCTCCTG GGCTGGGCGG GTGCCAAGAA GGTTCCTGTG          60

GTGGGGCCAG CGTTGGGCTA CATGATGGGA GGGACAGACA CCCGAGCGGC TGGAGCAGGT         120

CTGGGCACTG TCCCGAGGCA TTGAGGGAAG GGGCCGCAGC TGCAGCGAGT CCAGCCGAGG         180

CCTGCAGGCT GAGTTCCCCG GGCACAGCGG TGATGCCGAG TCACAGTGAG GAGAAGGGGA         240

GGGAGAGTGC ACTTCTGCTC AGTGCTGCCG AGATGGGGTG CCACCTGCCA TTAGGTCCTG         300

TTGCTCTTCA GAAGGAGGGA CAAGGAGCTC CTGGAAGTGG CTCACGCCAT CCCAGGGAAG         360

CCCAGGCTGA CCTGCAGGGT CAGCCTTGTC CCGGAGCAGG AGGCTGCAGT GCTCCTGGGT         420

GTGTGTCAGT GGTCACCAGT CCCTCTGGGC T                                        451

-continued (2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (xi) SEQUENCE DESCRIPTION: SEQ ID NO:6:

TTCTCCTGGG CTGGGCGG        18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (xi) SEQUENCE DESCRIPTION: SEQ ID NO:7:

ACTGACACAC ACCCAGGA        18

CYTOKINE RELATED TO HEMOLYTIC ANEMIA AND METHOD OF USE

This application is a continuation-in-part of the application which Ser. No. is 08/546,872 filed on Oct. 23, 1995.

BACKGROUND OF THE INVENTION

Polymerase chain reaction (PCR) is not restricted to DNA templates. RNA may also be amplified by PCR, because Taq polymerase possesses weak reverse transcriptase activity [1]. Since nonspecific PCR has been successfully exploited as a fingerprinting method and as a tool for polymorphism detection in genomic DNA [2,3], we have made use of nonspecific PCR to investigate alterations in gene expression in congenital hemolytic anemia.

The cellular integrity of the red blood cells depends on proteins that belong to four distinct functional systems: responsible for the repair of oxidative damage (pentose phosphate shunt-glutathione pathway), the system responsible for the transport of oxygen (hemoglobins), the system responsible for the cellular exchanges (membrane and cytoskeleton), and energy generation (glycolytic pathway). In each of these systems, mutations have been found that are responsible for hereditary hemolytic disorders. Among others, hereditary non-spherocytic anemia may be caused by deficiency of pyruvate kinase in the glycolytic pathway [4]. Hemolytic anemia occurs whenever the steady-state normal number of red cells is diminished, due to decreased stability. Since the bone marrow has the capability to increase its production of erythrocytes [5], hemolytic anemia is characterized by both increased hemolysis and increased erythropoiesis. Hence, the higher turnover rate of red blood cells is indicated by reticulocytosis and elevated bilirubinemia.

Using nonspecific PCR, we have obtained evidence that the expression of several genes is activated in blood cells four from patients with hereditary hemolytic anemia. Three are diagnosed with pyruvate kinase deficiency and one is of unknown cause. Two markers have been already identified and have been proposed to be human markers associated with hereditary hemolytic anemia [18]. We present here the genetic expression studies of marker B. This marker shows homology with bovine interferon α-A gene. Since interferon has a role as a differentiation factor in the erythroid cell lineage and is used as a therapeutic agent to treat hairy cell leukemia, marker B may be another related interleukin which may be used to develop pharmaceutical agents to be advantageously used in the treatment of hemolytic anemia caused inter alia by pyruvate kinase deficiency. This disease does not respond well to the well-known hematopoiesis growth factor, erythropoietin [21]. Marker A is, on the other hand, homologous to platelet-derived growth factor receptor (PDGFr). We still do not know if marker A is part of a DNA sequence encoding a receptor which responds to marker B or if marker A responds to another growth factor, like PDGF.

Even though the above two genes were identified as markers of hemolytic anemia, no specific role has been assigned thereto.

STATEMENT OF THE INVENTION

Beside a suggested role in erythropoiesis, we tested marker B in different blood cell populations. Preliminary assays have led us to assign at least one biological activity to this marker which we have called hemolytic anemia related factor (HMF). In accordance with the present invention, there is provided a method of enhancing hematopoiesis in a patient in need for such treatment which comprises the step of administering an hematopoietic dose of a hemolytic anemia related factor, hmf, which has the amino acid sequence defined in SEQ ID. NO: 4 to the blood of said patient.

In the above method, lymphoblastic activity is greatly enhanced by the presence of erythrocytes in the assay.

BRIEF DESCRIPTION OF DRAWINGS

FIG. 8. Analysis of pGEX-2TK recombinants for HMF. Clone 62 has been sequenced and shown to incorporate HMF in the right direction and in frame with glutathione transferase.

DESCRIPTION OF THE INVENTION

Materials and Methods

Patients

Venous blood was collected from one patient with hereditary nonspherocytic hemolytic anemia of unknown origin (G.Ga) and from four patients with pyruvate kinase deficiency and their families (Table 1). All had reticulocyte counts above 5%. Two had been splenectomized (G.Ga and A.Ca). Their enzymatic status was assessed using the method recommended by the International Committee for Standardization in Hematology [6]. Erythrocytes were separated from leucocytes on Ficoll-Hypaque density gradients (Pharmacia) and then purified from even traces of leukocytes and platelets, which contain contaminating isozymic $M_2$ pyruvate kinase, by liquid chromatography on a mixed microcrystalline and α-cellulose bed (Sigma). Pyruvate kinase was assayed, using the lactate dehydrogenase coupled assay in the dialyzed extracts at high phosphoenolyruvate concentration. The specific activity was the ratio of erythrocytic pyruvate kinase activity to hemoglobin content. The specific activity was not corrected for the half-life of the red blood cells. Therefore, in the homozygous patient MGa showed a higher pyruvate kinase specific activity than the heterozygous mother, as a consequence of the preservation of enzymatic activity in less aged cells.

DNA Studies

Crude DNA extracts were prepared from whole blood by dissolved cytoplasmic membranes, pelleting the nuclei and digesting them with proteinase K [7]. RNA-free extracts were obtained by treatment of crude extracts with ribonuclease A, phenol extraction, and ethanol precipitation [8]. PCR was targeted on exon 6 of human erythrocytic pyruvate kinase [9], with the oligonucleotides:

S (sense) 5'-AGCCCAGAGGGACTGGTGACC-3' SEQ ID NO: 1

A (antisense) 5'-CTTCACGCCTTCGTGGTTCTA-3' SEQ ID NO: 2

The reaction was conducted in 40 consecutive cycles of 1 min denaturation at 95° C., 1 min annealing at 60° C., and 2 min elongation at 70° C., in a volume of 100 µl containing 1 µM primers S and A and 5 U of Ampli-Taq (Perkin Elmer Cetus) in a Hypercell thermal cycler. The PCR amplification products were analyzed by gel electrophoresis on 3% NuSieve agarose. Discrete DNA bands were extracted on Zeta-probe membrane (Biorad), eluted and desalted on Centricon 30 (Amicon), and ligated in SmaI-restricted Bluescript KS$^+$ [10]. Competent XL1 cells were transformed and colonies were screened for recombinants. Positive recombinants of the appropriate insert size were sequenced by the Sanger dideoxy method.

PCR-amplified products and EcoRI-digested genomic DNA were analyzed by Southern blot. The agarose electrophoretic gels were blotted onto Zeta-probe membranes that were hybridized with recombinant Bluescript $^{32}$P probe labeled by the multiprime method. The blots were washed at high stringency (65° C., 0.1× Standard saline citrate, 0.5% sodium docecyl sulfate).

RNA Studies

Leukocytic and tissue RNA were isolated by acid guanidinium thiocyanate-phenol-chloroform extraction [11]. RNA (1 µg) preparations were denatured in glyoxal-dimethyl sulfoxide and electrophoresed in 1% formaldehyde-agarose [12]. The nucleic acids were transferred onto GeneScreen membranes. The Northern blot was hybridized with $^{32}$P probe labeled by the multiprime method and washed under stringent conditions.

Results

Figure 1:
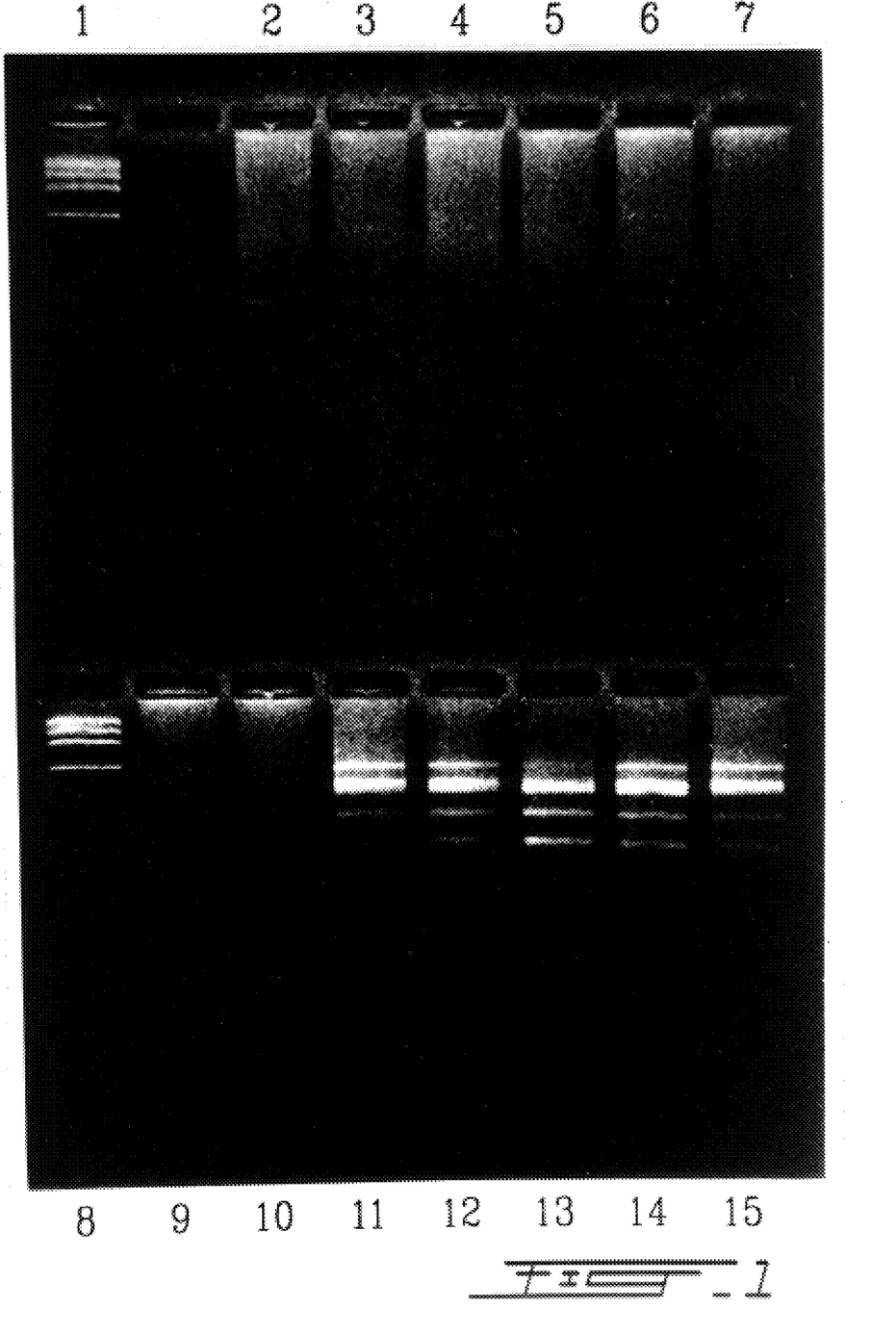
FIG. 1. PCR-amplified DNA markers specific for patients with hereditary hemolytic anemia. PCR products are analysed by gel electrophoresis on agarose NuSieve 3%. Lanes 1 and 8, HaeIII-digested φX174, molecular weight marker, lanes 2–9, control individuals; lane 10, patient N.Bo.; lanes 11 and 12, patient G.Ga.; lane 13, patient M.E.Du.; lane 14, patient M.Ga.; lane 15, patient A.Ca.
Figure 2:
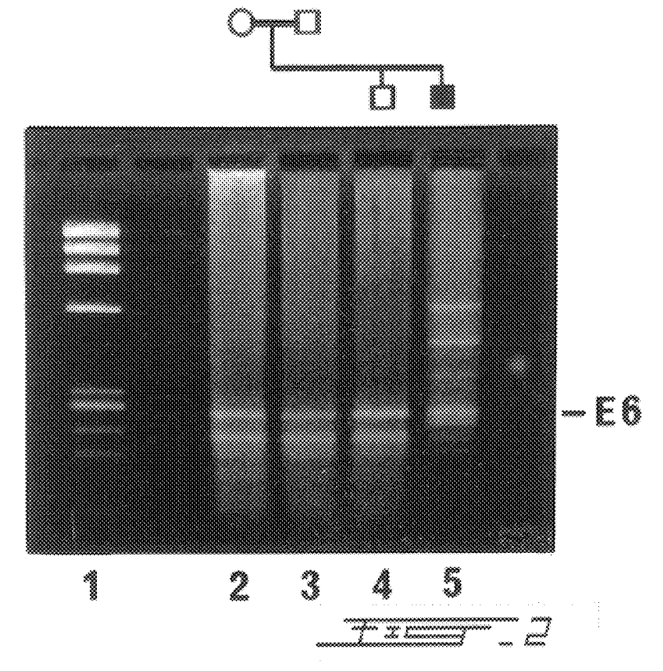
FIG. 2. Familial study of PCR-amplified DNA markers in a case of hereditary nonspherocytic hemolytic anemia due to pyruvate kinase deficiency. Lane 1, HaeIII-digested φX174; lane 2–5, respectively, mother, father, brother, and proband M.Ga; E6, position of exon 6 of pyruvate kinase L. PCR products are analysed by gel electrophoresis on agarose NuSieve 3%.

Characterization of Specific Misprimed PCR Products in Crude Leukocytic DNA from Hemolytic Patients Two genes code for pyruvate kinase, the M and the L genes. Erythrocytic pyruvate kinase is encoded by the L gene [13]. After PCR conditions were optimized for the specific amplification of exon 6 of the pyruvate kinase L gene, multiple bands were generated from the crude leukocytic DNA extracts of anemic patients only. Under sterile conditions, specific amplification of exon 6 is obtained by the "hot start" technique, using primers longer than 18-mer, and choosing an annealing temperature that is 5° C. below the fusion temperature of the primer-template duplexes [14]. Under these conditions, a multiple band pattern appeared in three of the four anemic patients tested. This pattern was absent in the seven healthy individuals tested (FIG. 1). Amongst the amplified bands, the pyruvate kinase band was still present in each case. It is a 270-bp PCR product that has been sequenced and shown to be identical to the published sequence [9]was still present in each case. In the family of patient M.Ga, whose asymptomatic parents were found to be heterozygous for pyruvate kinase deficiency (Table 1), the multiple band pattern was obtained only for the hemolytic patient (FIG. 2).

Figure 3A:
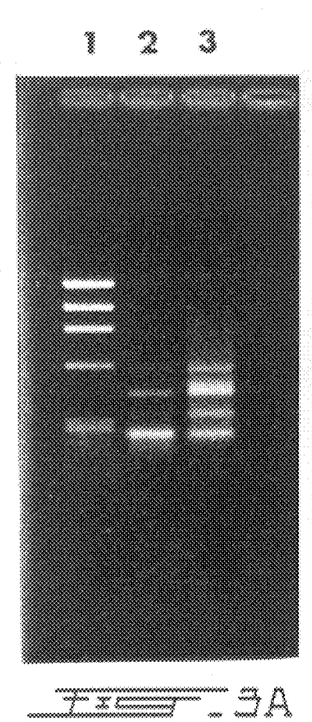
FIGS. 3A–3B Southern blot analysis of PCR-amplified DNA markers generated with primer S only. (A) Agarose electrophoresis of the PCR products: lane 1, HaeIII-digested φX174; lane 2, PCR products generated from 0.5 µg of leukocytic DNA of a normal individual; lane 3, PCR products generated form 0.5 µg of leukocytic DNA of patient G.Ga. (B) Southern blot of A, hybridized with $^{32}$P-labeled probe HUMDNAMB crude leukocyte extracts contaminated with mRNA. A. PCR products are analysed by gel electrophoresis on agarose NuSeive 3%. B. After transfer on nylon membrane, the PCR products are hybribized with $P^{32}$-labeled HUMDNAMB. HUMDNAB is overexpressed in a patient with hemolytic anemia compared to a normal individual.
Figure 3B:
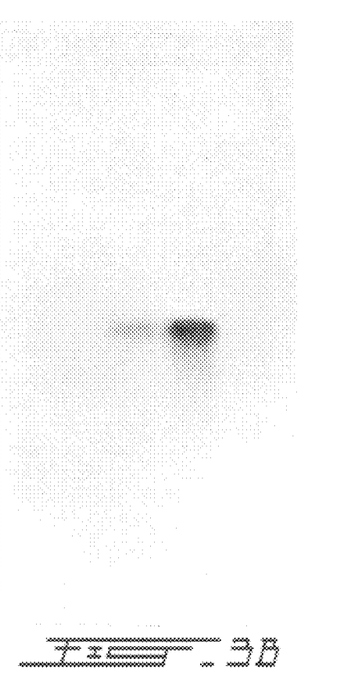

At that point, the mechanism by which extra PCR bands were cogenerated with pyruvate kinase exon 6, only in anemic patients was not clear. It could possibly originate infections secondary to hemolytic anemia, from DNA recombination related to pyruvate kinase deficiency, or the presence of specific RNA templates. We observed that the extra PCR products were generated when using both primers S (SEQ ID NO: 1) and A (SEQ ID NO: 2), in anemic patients alone, but that it was generated in every individual, using primer S (SEQ ID NO: 1) only. FIG. 3 shows that under these conditions, the expected amplification product was present in both a healthy individual and a patient with hemolytic anemia, but its dosage, as measured by Southern blot, was increased about five times in the diseased patient. A study of the intensity of the ethidium-colored HUMD-NAMB PCR band, at various PCR cycle numbers, confirmed that the dosage is about five times more elevated in anemic patients. The same increase in dosage was found in patients M.E.Du and G.Ga.

TABLE 1

Pyruvate Kinase Activity in Erythrocytes of Patients with Congenital Hemolytic Anemia

| Family | Patient | Age (years) | Specific pyruvate kinase activity (% of mean normal value) | | |
|--------|---------|-------------|---------|--------|--------|
|        |         |             | Proband | Mother | Father |
| F25    | G.Ga    | 25          | 99      | NA$^a$ | NA     |
| F10    | M.E.Du  | 3           | 52      | NA     | NA     |
| F27    | A.Ca    | 6           | 16      | 25     | 27     |
| F35    | N.Bo    | 8           | 55      | 59     | 76     |
| F41    | M.Ga    | 8           | 57      | 6      | 48     |

$^a$NA, not available

Since the HUMDNAMB PCR product was amplified from primer (SEQ ID NO: 1) alone (as sense and anti-sense primer S S in every individual tested but at a higher dosage in anemic patients, we could eliminate some of the hypotheses proposed to explain the extra bands: they were not generated by an infectious vector present only in the patients and were not the product of disease-specific DNA recombination. We assumed that an increased number of HUM-DNAMB templates could explain our results. Because it was previously reported that the Taq polymerase had reverse transcriptase activity and that abundant messenger RNAs could be amplified by PCR [1], we tested the possibility that crude leukocytic DNA extracts could be contaminated by HUMDNAMB messenger RNA. Indeed, purified RNase-treated leukocytic DNA extracts of anemic patients lost the ability to generate extra PCR bands with pyruvate kinase primers S (SEQ ID NO: 1) and A (SEQ ID NO: 2). We then concluded that the appearance of the PCR HUMDNAMB product during exon 6 pyruvate kinase L amplification was due to overwhelming competition by an increased number of copies of HUMDNAMB messenger RNA templates contaminating the leukocytic genomic extract of affected individuals and that the expression of HUMDNAMB mRNA was increased in hemolytic conditions.

Overexpression of HUMDNAMB in Leukocytic Extracts of More Patients with Hemolytic Anemia The previously obtained series of 5 patients and 10 controls showing overexpression of HUMDNAMB in patients with hemolytic anemia has been expanded. The blood of 12 patients and 20 control individuals was collected in EDTA tubes. Leukocytes were separated on discontinuous Ficoll HiPaque gradients (Pharmacia). Total RNA was extracted from the leukocytes with TRI reagent, following the instructions of the manufacturer (Molecular Research Center Inc.). The first strand of cDNA was synthetised with superscript reverse transcriptase using polyT (Life Sciences) and HUMDNAMB cDNA was quantitatively amplified by PCR using primers as defined in SEQ ID NO: 1 and SEQ ID NO: 2. The density of the bands obtained on agarose gel electrophoresis were measured by densitometry. The expression of HUMDNAMB was found to be significantly elevated in patients: 15±1.5, compared to controls: 1±0.5 which mean is taken as a unit.

Genetic Study of the Hemolysis-related Factor HUMDNAMB

The bands that differed between patients and controls following PCR amplification of exon 6 of the erythrocytic pyruvate kinase were cloned and sequenced. One of these bands, DNA marker B (HUMDNAMB, GenBank accession number M-64701), is a 451-bp open reading frame that has been described recently (Table 2).

TABLE 2

Nucleotide and Deduced Amino Acid Sequence of Human DNA Marker B[a] (SEQ ID NOS: 5 and 4, respectively)

| | SEQ ID NO: |
|---|---|
| 1<br>AGCCCAGAGGGACTGGTGACCCTTCTCCTGGGCTGGGCGGGTGCCAAGAAGGTTCCTGT<br>  ProArgGlyThrGlyAspProSerProGlyLeuGlyGlyCysGlnGluGlySerCys<br>  1 | 5<br>4 |
| 60<br>  GGTGGGGCCAGCGTTGGGCTACATGATGGGAGGGACAGACACCCGAGCGGCTGGAGCAGG<br>  GlyGlyAlaSerValGlyLeuHisSerGlyArgAspArgHisProSerGlyTrpSerArg<br>  20 | |
| 120<br>  TCTGGGCACTGTCCCGAGGCATTGAGGGAAGGGGCCGCAGCTGCAGCGAGTCCAGCCGAG<br>  SerGlyHisCysProGluAlaLeuArgGluGlyAlaAlaAlaAlaAlaSerProAlaGlu<br>  40 | |
| 180<br>  GCCTGCAGGCTGAGTTCCCCGGGCACAGCGGTGATGCCGAGTCACAGTGAGGAGAAGGGG<br>  AlaCysArgLeuSerSerProGlyThrAlaValMetProSerHisSerGluGluLysGly<br>  60 | |
| 240<br>  AGGGAGAGTGCACTTCTGCTCAGTGCTGCCGAGATGGGGTGCCACCTGCCATTAGGTCCT<br>  ArgGluSerAlaLeuLeuLeuSerAlaAlaGluMetGlyCysHisLeuProLeuGlyLeu<br>  80 | |
| 300<br>  GTTGCTCTTCAGAAGGAGGGACAAGGAGCTCCTGGAAGTGGCTCACGCCATCCCAGGGAA<br>  ValAlaLeuGlnLysGluGlyGlnGlyAlaProGlySerGlySerArgHisProArgGlu<br>  100 | |
| 360<br>  GCCCAGGCTGACCTGCAGGGTCAGCCTTGTCCCGGAGCAGGAGGCTGCAGTGCTCCTGGG<br>  AlaGlnAlaAspLeuGlnGlyGlnProCysProGlyAlaGlyGlyCysSerAlaProGly<br>  120 | |
| 420<br>  TGTGTGTCAGTGGTCACCAGTCCCTCTGGGCT<br>  CysValSerValValThrSerProSerGly<br>  140 | |

[a]Underlined nucleotides correspond to the direct and complementary sequences of primer S SEQ ID NOS: 1) and 3).
[b]Overlined nucleotides correspond to the direct and complementary sequences used to amplify the same sequence prior to cloning in the pGEX-2T plasmid.

Figure 4:
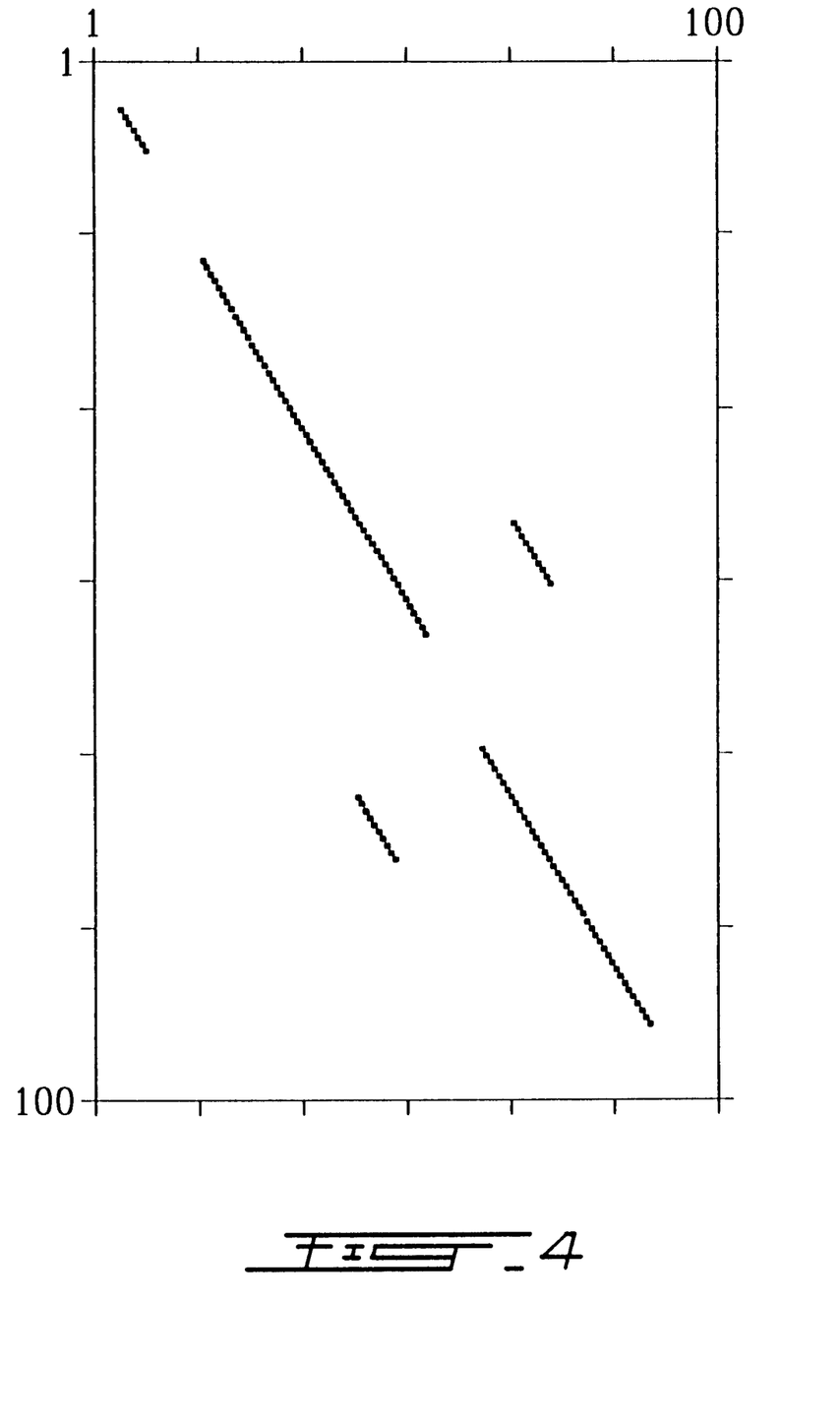
FIG. 4. Protein homology plot of human hemolysis-related factor HUMDNAMB (horizontal) and bovine interferon-αA (vertical). The plots are constructed using a window of six amino acids and five matching amino acids.

The nucleotidic sequence 303–416 of HUMDNAMB and its entire sequence show 63 and 48% homology, respectively, with bovine interferon α-A [15]. Another human interferon exhibiting the same property, interferon ω, bears no homology with HUMDNAMB. The open reading frame codes for a protein with a glycine rich N-terminal domain, a proline-rich C-terminal domain, and an alanine-serine-lysine rich central domain. Its hydrophobicity plot suggests the same folding pattern as for other interferons. It has no extended homology with any other protein (verified at NCBI using the BLAST network service—March 1997). It possesses a consensus interferon basic motif. Several features indicate that HUMDNAMB encodes a larger protein than interferons. The 5' end of the cloned sequence has five coding nucleotides upstream of the first ATG codon of interferon, with no ATG codon in the vicinity. We compared the deduced amino acid sequence of HUMDNAMB with the primary structure of bovine interferon α-A, using Prosis matrix analysis (FIG. 4). It is noticeable that the first amino acids, which correspond to the beginning of the interferon molecule, where its signal peptide is located, belong to a region of a lesser homology than the rest of the sequence. These features suggest that the HUMDNAMB protein has an extended $NH_2$-terminal region as compared to with interferon.

The extremities of HUMDNAMB incorporate the direct and complementary copies of primer S (Table 2), indicating that primer S (SEQ ID NO: 1) anneals at three distinct locations of the genomic template, one in pyruvate kinase exon 6 and two in HUMDNAMB. It follows that one or several mismatches have probably occurred, given the abundance of the 21-mer sequence, calculated on the probabilistic assumption that the genome is generated by chance [16]. This phenomenon is usually encountered with primers with a high GC content, such as primer S. It explains why HUMDNAMB may be amplified in competition with pyruvate kinase exon 6.

Figure 5:
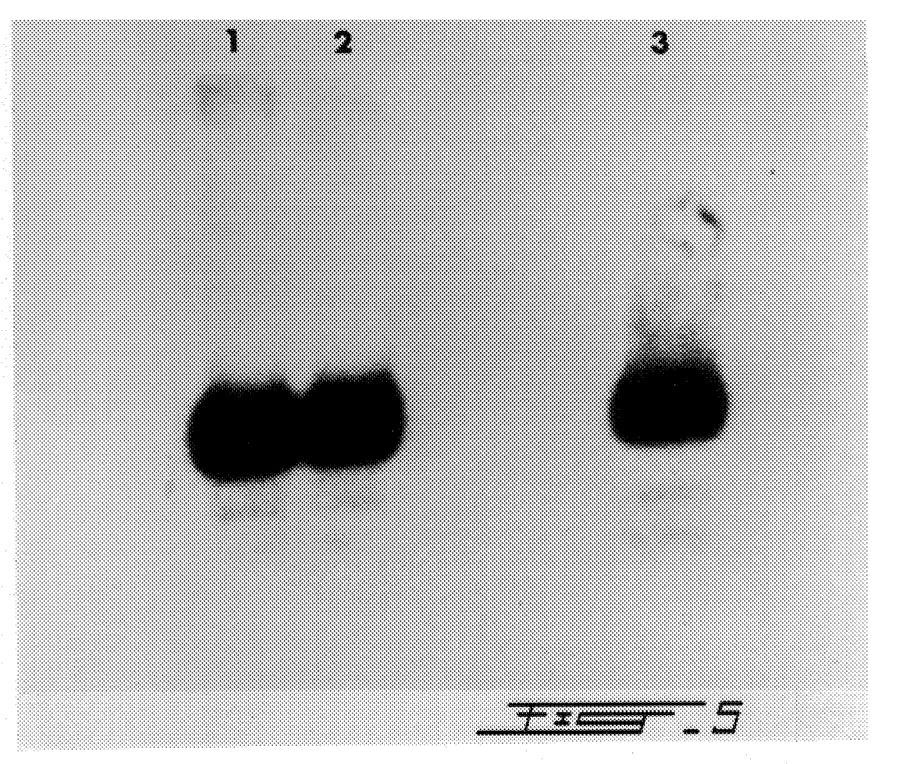
FIG. 5. Southern blot analysis of genomic DNA hybridized with $^{32}$P-labeled HUMDNAMB. Lanes 1 and 2, 5 µg of EcoRI-digested leukocytic DNA from a normal individual; lane 3, 1 µg of EcoRI-digested leukocytic DNA from patient M.E.Du. The positive band migrates at a position corresponding to a molecular size of 9 kb.

We tested the presence of HUMDNAMB in a genomic blot. The purified leukocytic DNA was digested with EcoRI, electrophoresed, blotted, and probed with labelled HUMDNAMB probe. A single and identical restriction fragment was obtained in a patient and in a control, with an apparent molecular size of 9 kb (FIG. 5).

Figure 6:
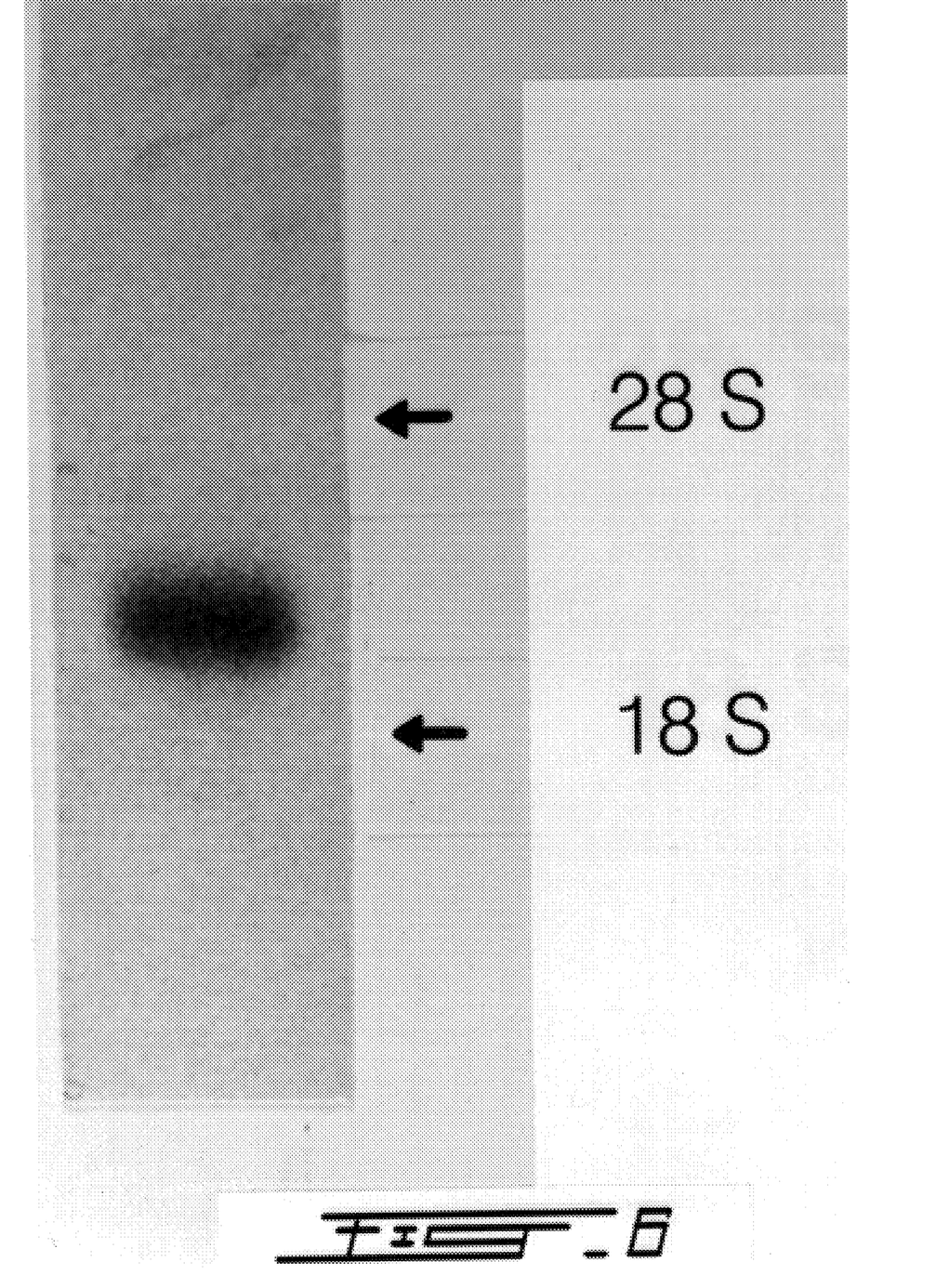
FIG. 6. Northern blot analysis of 10 µg of leukocytic RNA extract of a healthy donor, hybridized with $^{32}$P-labeled HUMDNAMB probe.

Northern blot analysis of leukocytic total RNA, with labelled HUMDNAMB showed a HUMDNAMB messenger RNA of approximately 2 kb (FIG. 6). The HUMDNAMB mRNA is notably larger than the 1.2-kb interferon-α mRNA [17], corroborating the indications from the cloned fragment that the HUMDNAMB protein may be larger than interferons. The presence of HUMDNAMB mRNA was also detected in human fetal liver and human fetal intestine. It was not detected in chicken adrenal glands (results not shown). This gene will be hereinafter referred to as a hemolytic anemia related factor (hmf).

Studies of the Hemolysis-related Factor HUMDNAMA (GenBank Accession Number M64700)

Another PCR band of 346 bp in length has 54% homology with the 3' non-coding region of human PDGF receptor cDNA.

Cytokine Activity of the Hemolytic Anemia Related Factor (HMF)

Detection of Transcripts Specific for Hemolytic Anemia due to Pyruvate Kinase Deficiency PCR fingerprints of leukocytic extracts have brought up the existence of two transcripts which appear specifically overexpressed in three of four patients with hemolytic anemia due to pyruvate kinase deficiency, as compared to ten normal controls [18]. The cDNA fragments, obtained by PCR amplification with non-specific primers, have been cloned in the bacterial plasmid Bluescript (Stratagene). Their sequences have been registered in GenBank (Table 3).

TABLE 3

Novel gene products detected in PCR fingerprints of blood from patients with pyruvate kinase deficiency

| Human DNA markers | A | B (hmf) |
| --- | --- | --- |
| GenBank accession number | M64700 (1989) | M64701 (1994) |
| Homology | platelet-derived growth factor receptor (PDGFR) | interferon Aα (INF) |

It is possible that the transcripts are not strictly of leukocytic origin, because the buffy coat of the cells is coloured in red, indicating a contamination by reticulocytes, which are particularly abundant in patients affected by hemolytic anemia.

Expression of a Glutathione-S-transferase Fusion Protein with HMF

A. hmf Subcloning in pGEX-2TK

Figure 7:
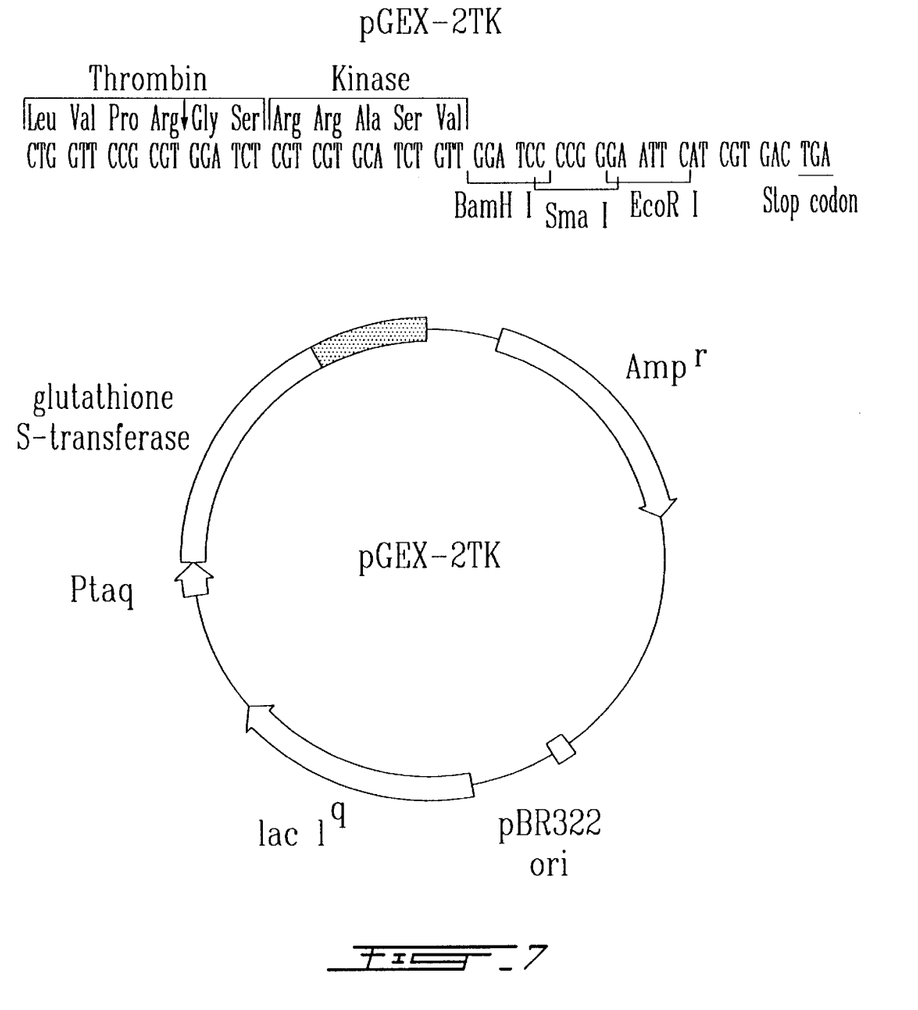
FIG. 7. Description of the expression bacterial vector pGEX-2TK.

Expression of the hmf protein has been obtained in the prokaryotic vector pGEX-2TK (Pharmacia). The vector expresses a fusion protein with glutathione-S-transferase (GST), which can be easily purified by affinity chromatography on glutathione-Sepharose 4B. The GST gene is under the control of the tac promoter and is inducible by IPTG, and contains an ATG and a transcription termination signal. It is flanked by a ribosome binding site. Cloning into the vector is possible in the three reading frames, by a multiple cloning site BamH1-Sma1-EcoR1. The GST protein contains a thrombin cleavage site to allow for the hydrolysis of the fused product. The protein contains also a cAMP-dependent protein kinase phosphorylation site, which allows $^{32}P$ labelling (FIG. 7).

The Sma1 cloning site has been used because it generates blunt ends. A 408 bp PCR fragment in the appropriate reading frame was amplified from the original Bluescript clone, using the following synthetic primers (which position is shown in Table 2):

HUMDNAMBS: 5'TTCTCCTGGGCTGGGCGG3'   DEQ ID NO:6
HUMDNAMBA: 5'ACTGACACACACCCAGGA3'   SEQ ID NO:7

The overhangs were digested by treatment with Mung bean nuclease. The vector was digested with Sma1 and dephosphorylated with calf intestine alkaline phosphatase, prior to ligation with the PCR fragment. Transformation was achieved in competent cells from *E. coli* XL-1 (Stratagene), by the method of Hanahan. Clones were selected on ampicillin and tested for the size of the insert by EcoRI-EcoRV double digestion. Wild type clones gave fragments of 3155 and 1840 bp, whereas positive clones had fragments of 3155 and 2222 bp, as expected (FIG. 8). The orientation of the insert was asserted by restriction map. Clone 62 obeyed the criteria of the cloned hmf and its sequence was confirmed by DNA sequencing.

Expression of HMF

Bacteria containing the wild type plasmid pGEX-2TK or the HMF-GST fusion gene plasmid PGEX-2TK-62 were grown at 37° C. in a medium 2YT-glucose-ampicillin, until the optical density of 600 nm reached 1 unit. The protein was induced with 0.1 mM IPTG for 2 hours. The bacteria were isolated by centrifugation, resuspended in ¹⁄₂₀th of the initial volume in phosphate buffer saline (PBS) containing 3%

Figure 9:
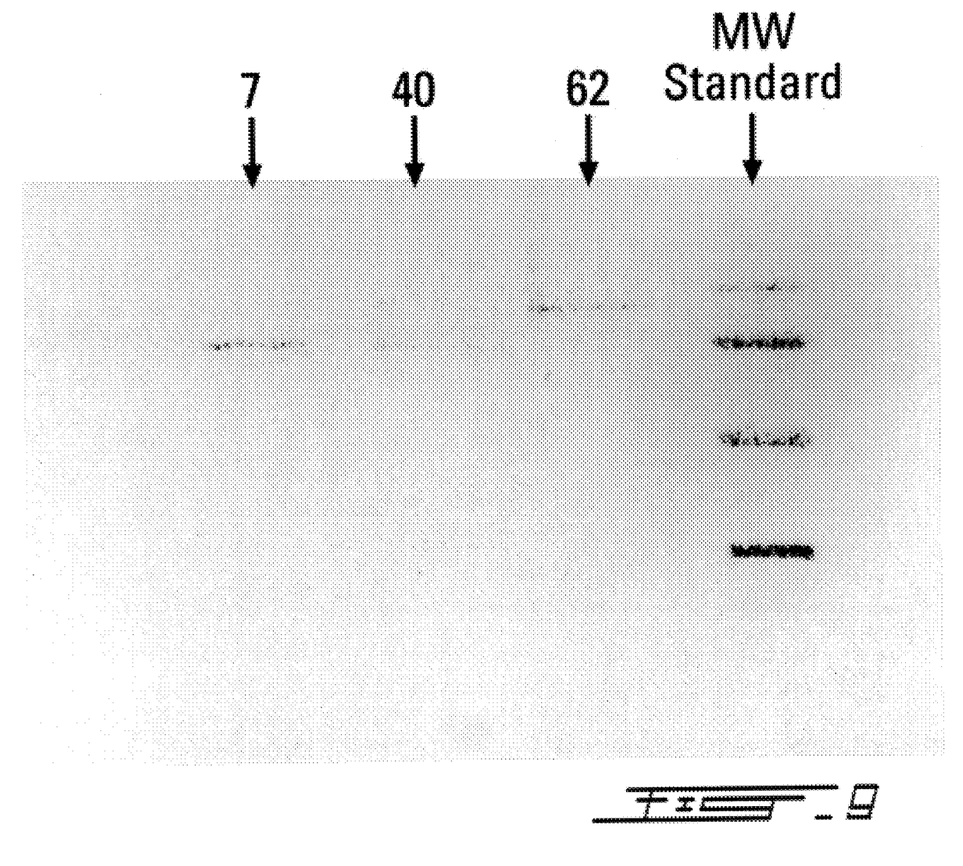
FIG. 9. Analysis of the proteins expressed by pGEX-2TK recombinants, with polyacrylamide gel electrophoresis. Clone 62 expresses the fusion protein HMF-glutathione transferase.

Triton X-100, and sonicated. The bacterial cell debris were eliminated by centrifugation and the GST protein was purified from the supernatant by column affinity chromatography on glutathione-Sepharose 4B, using PBS as washing buffer and 30 mM Tris, pH 8.0, 10 nM glutathione, as elution buffer. Proteins were analysed by polyacrylamide gel electrophoresis in denaturing (SDS) and reducing (mercaptoethanol) conditions (FIG. 9).

Biological Activity of HMF

Once established that HMF was overexpressed in patients having hereditary hemolytic anemia, and knowing that, in these patients, hemolysis is compensated by an increase in red cells synthesis, by a factor of approximately 5× to 10 × [5], it was conceivable that HMF may have a role, either in hematopoiesis, or in the disposal of pathological cells. The biological effect of HMF was thus investigated in blood cells.

Effect on Erythroid Lineages

The erythroid cells which are competent for proliferation and differentiation, are the chorionic embryonic cells, and the bone marrow and blood erythroid cells, originating from stem cells and giving rise to successively more differentiated and more committed cell types: pluripotent progenitors P-GEMM, and committed precursors, BFU-E and CFU-E. Since we had no access to these specialized cell populations, we tested HMF on stable human cell lineages, derived from erythroleukemia immortalized cells, such as K562 and HEL. These cell lines are commonly used as in vitro models of differentiation with erythropoietin, a cytokine which induces the appearance of proerythroblasts in BFU-E and CFU-E colonies, HMF had no immediate effect on these cell lines. This negative result does not exclude that the possibilities that HMF: may act only on natural cell populations, its effect would take place at anterior or posterior stages, or that its effect would be dependent on another cytokine acting synergistically, its effect would not be measurable, or if it had a stabilizing effect, etc. Other tests based on the presence of a HMF receptor are currently under investigation.

B. Effect on Leukocytes Lineages

Each leukocytic fraction was isolated from the peripheral blood of one donor, by Ficoll-Paque density gradient. The leukocytes were washed and resuspended in RPMI medium (Gibco), then incubated at 37° C. under $O_2$—$CO_2$. Aliquots of the culture were taken at various intervals of time, treated with trypan blue and the cells were counted in a hemacymeter. Any cytotoxic activity is shown by a decrease of viable cells compared to the expected values, any blastic activity is shown by an increase of viable cells.

The results shows that leukocytes are incubated in RPMI without serum, or without supplementation with growth factors and cytokines, gradually die. After one day, 50% of the cells maintain trypan blue exclusion, 25% after two days, 15% after three days, 9% after four days and after seven days the whole population completely vanished. The biological activity of a cytokine is demonstrated by a disturbance of the gradual decrease of leukocytes viability with time. The addition of the fusion protein HMF-GST shows two kinds of disturbances: an early cytotoxic phase and a delayed lymphoblastic phase.

Figure 10:
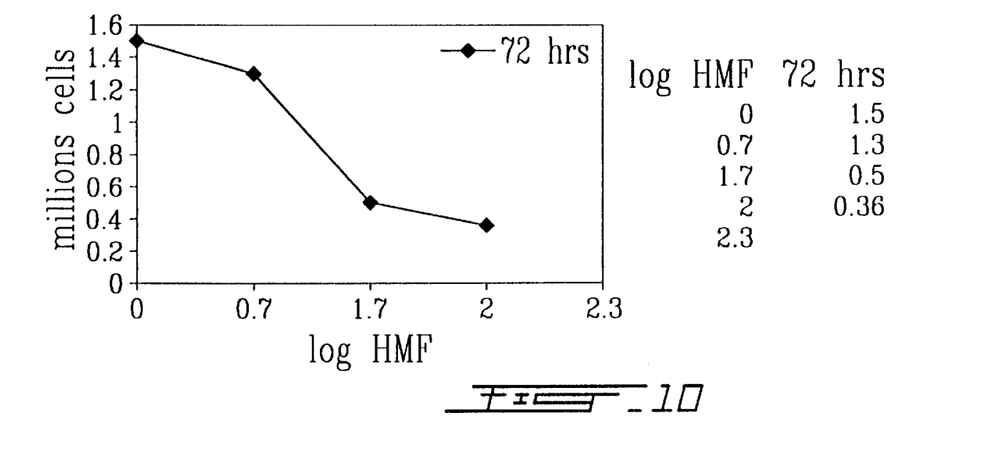
FIG. 10. Cytotoxic activity of the HMF-glutathione transferase fusion protein. The immediate effect of HMF on cultured leukocytes, is a decrease in viable cells, tested by trypan blue exclusion.
Figure 11:
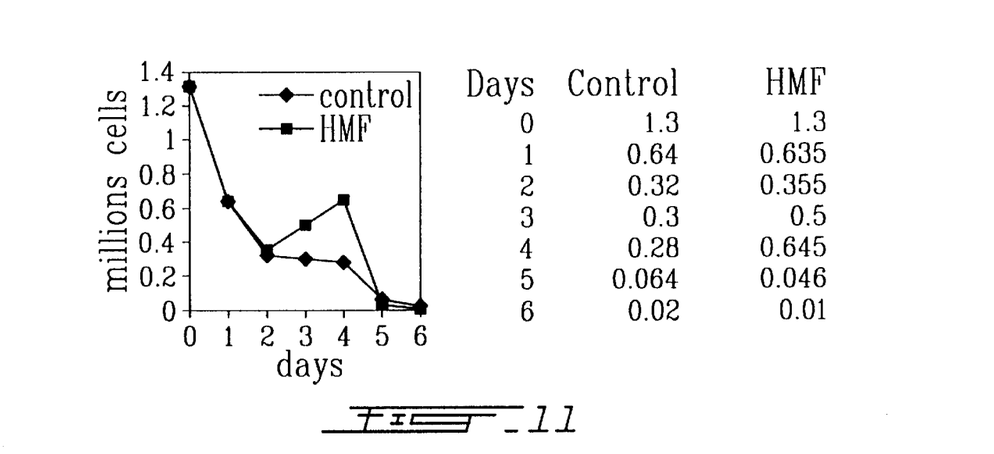
FIG. 11. Delayed lymphoblastic activity of the HMF-glutathione transferase fusion protein in mixed culture of leukocytes. Viable cells are counted in a hemacymeter and lymphoblasts are identified by light microscopy with Wright's staining.

In the first 2–3 days, addition of HMF-GST ranging between 0–100 ng per flask results, in some of the donors but not all of them, in a decrease of viable cells which is dose-dependent (FIG. 10). The lack of response in certain donors may be due to a different composition of the leukocytes and an alteration of their interaction. The leukocytes are composed of a mixed population of 50–75% neutrophils, 20–45% lymphocytes, 5–10% monocytes and few basophils [25]. If the target cells are present at a lower concentration inducing less activity, the cytotoxic effect may be blurred in the consecutive blastic phase (FIG. 11).

After 3 days, of initial 100 ng per flask HMF-GST treatment, the cell population shows always a huge cellular proliferation (FIG. 11) and the number of viable cells increase by a factor of 2–3. GST alone at the same dose has a slighter effect. An increase of the viable cells in a continuous culture must come from a proliferation of the remaining cells. A Wright's stain shows mostly lymphoblasts. The delayed lymphoblastic effect supposes that HMF-GST does not act directly on lymphocytes, but on other cells, which in turn secrete other cytokines with lymphoproliferative activity. It is known for instance, that the parent interferon alpha stimulates interferon gamma which activates monocytes. In turn, the monocytes produce interleukine-2(IL-2), a lymphoblastic cytokine. The lymphoblastic activity may be synergistic with other lymphoblastic substances like lectins [19]. It is possible that GST has an activity by itself which is synergistically enhanced by HMF.

It is well known that interferon which binds to monocytes, activates them in order to produce other cytokines, such as interleukine-2 which provokes a lymphoblastic activity like the one observed with HMF.

Leukocytes isolated on Dextran and washed with phosphate-buffer-saline (PBS) have been incubated with HMF-glutathione transferase fusion protein, glutathione transferase or PBS alone, in the presence of 5 μM suramin. The cells were incubated 1 hour at 4° C. washed, then incubated with goat anti-glutathione transferase antibodies 0.5 hour at 4° C., washed again and incubated with swine anti-goat FITC antibodies 0.5 hour at 4° C. Flux cytometry analysis of cells separated on CD4 and CD14 discrimination showed that HMF-glutathione transferase binds to monocytes to a greater extent than GST alone (data not shown). This result, along with the delayed lymphoblastic activity, support a mechanism of action of HMF similar to the mechanism of interferon.

We tested also the effect of HMF on a reconstituted mixture of leukocytes and red blood cells (Table 4). The data show that there is a presentation effect of the red cells, which enhances the lymphoblastic activity of HMF receptor on their surface.

TABLE 3

Potentiation by red blood cells, of the lymphoblastic activity of HMF

| Incubation time | Lymphocytes + GST | Lymphocytes + GST – HMF | Lymphocytes + RBC GST – HMF |
|---|---|---|---|
| 2 days | 332000 | 274000 | 282000 |
| 3 days | 200000 | 426000 | 960000 |

GST and GST-HMF doses are 100 ng per flask.

Table 3 also shows that HMF has a slight cytotoxic effect (number decreased by 20% compared to control) for the first two days, which cytotoxicity is not affected by the presence of erythrocytes. By day 3, the number of control cells still decrease while the number of HMF-treated cells doubles (it resembles results of FIG. 11). Again, the lymphoblastic activity of HMF is very clear and it is potentiated by erythrocytes.

Discussion

The study of genes that are selectively expressed in specific disease states is helpful in understanding their pathophysiology. It is particularly important in the case of genetic diseases like hereditary hemolytic anemia, in which identical mutations often lead to various degrees of severity in the phenotype. In order to focus on the pertinent genetic background, we devised a PCR fingerprinting method for messenger RNAs. Specific amplification patterns were generated from leukocyte mRNAs of patients with hereditary hemolytic anemia. The PCR competing products, which appear in hemolytic patients and not in normal individuals or in heterozygous carriers of pyruvate kinase deficiency, were cloned, sequenced, and shown to be unrelated to pyruvate kinase L or to other genes involved in congenital hemolytic anemia. This study focuses on one of these hemolysis-related factors.

HUMDNAMB (hmf) is part of a new gene. Our results show that this new gene encodes a protein structurally related to type I interferon. hmf is expressed in human leukocytes, fetal intestine, and fetal liver. The size of the corresponding mRNA suggest that the protein could be larger than other human interferons. One may speculate about the function of HMF from the structural and circumstantial evidence. The clinical background that precluded HMF discovery suggests a role for this factor in the compensation mechanism that takes place in patients suffering from hemolytic anemia. Indeed, recent evidence showed that interferons may play the role of differentiation and growth factors in regulating normal hematopoiesis. Type I interferons, for example, stimulate the proliferation of non-lymphoid cell types from hematopoietic stem cells originating from the peripheral blood of patients with hairy cell leukemia [19]. The interferon-related protein HMF is a possible candidate for analogous functions. Hemolytic anemia also induces various sources of stress in patients, such as jaundice and hemochromatosis [20]. Expression of type I interferons has been shown to be stimulated under stress, and a protein like HMF, which bears homology with interferons, could be similarly regulated.

Because the severity of the disease is highly variable in patients with identical mutations and HMF expression has been shown to be elevated only in three of four anemic patients, hmf is a candidate gene for studying the influence of the genetic background on the phenotype in hereditary hemolytic anemia.

HMF is an interferon-like substance with an interferon-like activity. hmf has a nucleic acid homology of 48% with bovine interferon A-alpha, and in ⅓ of the sequence, the homology is 63%. HMF has a protein homology with bovine interferon A-alpha demonstrated by matrix homology. Interferons alpha and beta (type 1) are known to inhibit the replication of some hematopoietic cells [19]. The cytotoxic phase of HMF may be directly related to these properties. Type 1 interferons are known to induce interferon gamma which has a lymphoblastic activity [27,28]. HMF has a similar lymphoblastic activity in mixed leukocyte cultures.

Gamma interferon also plays an important role in monocytes' activation which differentiate in macrophage. Monocytes' activation and differentiation into macrophages have been implicated in many blood pathologies. (i.e. clearance of senescent red blood cells; secretion of interleukin-1 (IL-1), a key agent for body defense of homeostasis). The multiple activities of IL-1 include stimulation of IL-2 T-cells secretion and proliferation, stimulation of granulocyte-macrophage colony stimulating factor (GM-CSF) secretion in the bone-marrow, which in turn play a role in the proliferation of the erythrocytic lineage [25]. The interferon-like properties of HMF imply that the overexpression of HMF in patients with hemolytic anemia is related to the conditions of the patients, who experience increased erythropoiesis and increased red cells clearance.

Conclusion

We have identified a novel cytokine, HMF, which occurrence and action are located in blood cells. Its mechanism of action and its purpose remain still to be clarified, HMF, has probably an interesting therapeutic potential since other recombinant human cytokines, like interferon α, interferon γ and interleukin 2, are in the process, or have been marketed by pharmaceutical companies.

HMF is a marker of hemolytic anemia, and as such could play a role in its treatment. Since it may be a compensation factor, HMF could find a use for enhancing the production of erythrocytes in patients in need of such treatment. Since HMF has shown a lymphotoxic activity, it may be also useful in the treatment of patients wherein such cytotoxic activity is desirable, particularly in the case of anemia (a conventional therapeutic strategy for treating anemia consists of decreasing the blood cell population). Therapeutic doses may be adjusted for each method. It also has an in vitro lymphoblastic activity, a property which may well appear also in vivo. Moreover, reports have been made about three patients with pyruvate kinase deficiency, who developed myelomonocytic leukemia [22–24]. If true, applications may also be sought in the treatment of disorders associated with myeloid lineages. The search for biological activities is not completed and other interesting properties may soon be discovered.

If HMF is involved in leukemia, it is therefore expected that new drugs may be developed therefrom, which drugs may be useful in enhancing the blood erythrocytes counts and in preventing or stopping the development of leukemia. On the other hand, since lymphoblastic activity may be useful in treatment of immunodeficient state, HMF as such may find utility in the treatment of such diseases.

REFERENCES

1. Tse, W. T., Forget, B. G. (1990) Reverse transcription and direct amplification of cellular RNA transcripts by Taq polymerase. *Gene* 88, 293–296.
2. Welsh, J., McClelland, M. (1990) Fingerprinting genomes using PCR with arbitrary primers. *Nucleic Acids Res.* 18, 7213–7218.
3. Williams, J. G. K., Kubelik, A. R., Livak, K. J. Rafalsky, J. A., Tingey, S. V. (1990) DNA polymorphisms amplified by arbitrary primers are useful as genetic markers. *Nucleic Acids Res.* 18, 6531–6535.
4. Valentine, W. N., Tanaka, K. R., Paglia, D. E. (1989) Pyruvate kinase and other enzyme deficiency disorders of the erythrocytes. *In Metabolic Basis of Inherited Disease* (C. R. Scriver, A. L. Beaudet. W. S. Sly, and D. Vallee, eds) McGraw-Hill, New York, 2341–2365.
5. Crosby, W. H., Akeroyd, J. H. (1952) Limit of hemoglobin synthesis in hereditary hemolytic anemia: its relation to the excretion of bile pigment. *Am. J. Med.* 13, 273–283.
6. Miwa, S., Boivin, P., Blume, K. G., Arnold, H., Black, J. A., Kahn, A., Staal, G. E. J., Nakashima, K., Tanaka, K. R., Paglia, D. E., Valentine, W. N., Yoshida, A., Beutler, E. (1979) International Committee of Standardization in Haematology. *Br. J. Haematol* 43, 275–286.
7. Higuchi, R., Saiki, R. K. (1989) Simple and rapide preparation of samples for PCR. In *PCR Technology, Principles and Applications for DNA amplification* (H. A. Erlich, ed) Stockton Press, New York, 31–38.
8. Old, J. M. (1986) Fetal DNA analysis. *In Human Genetic Diseases, a Practical Approach* (K. E. Davies, ed) IRL Press, Washington, D.C. Chapter 1, pp.1–17.
9. Kanno, H., Fujii, H., Hirono, A., Miwa S. (1991) cDNA cloning of human R-type pyruvate kinase and identification of a single amino acid substitution (Thr$^{SM}$®$^{P}$-Met) affecting enzymatic stability in a pyruvate kinase variant (PK Tokyo) associated with hereditary hemolytic anemia. *Proc. Natl. Acad. Sci. USA* 88, 8218–8221.
10. Sambrook, J., Fritch, E. F., Maniatis, T. (1989) *Molecular Cloning.* Cold Spring Harbor Laboratory Press, Cold Spring Harbor, N.Y., 1.3–1.101.
11. Chomczynski, P., Sacchi, N. (1987) Single-step method of RNA isolation by acid guanidinium thiocyaniate-phenol-chloroform extraction. *Anal. Biochem.* 162, 156–159.
12. Thomas, P. S. (1980) Hybridization of denatured RNA and small DNA fragments transferred to nitrocellulose. *Proc. Natl. Acad. Sci. USA* 77, 5201–5205.
13. Noguchi, T., Yamada, J., Inoue, H., Matsuda, T., Tanaka, T. (1987) The L- and R-type isozymes of rat pyruvate are produced fron a single gene by use of different promoters. *J. Biol. Chem.* 262, 14366–14371.
14. Erlich, H. A., Gelfand, D., Sninsky, J. J. (1991) Recent advances in the polymerase chain reaction. *Science* 252, 1643–1651.
15. Velan, B., Cohen, S., Grosfeld, H., Leitner, N., Shafferman, A. (1985) Bovine interferon α genes: structure and expression. *J. Biol. Chem.* 260, 5498–5504.
16. Thein, S. L., Wallace, R. B. (1986) The use of synthetic oligonucleotides as specific hybridization probes in the diagnosis of genetic disorders. *In Human Genetic Diseases* (K. E. Davies, ed) IRL Press, Washington, D.C., 33–50.
17. Tovey, M. J., Streuli, M., Gresser, I., Gugenheim, J., Blanchard, B., Guymarho, J., Vignaux, R., Gigou, M. (1987) Interferon messenger RNA is produced constitutively in the organs of normal individuals. *Proc. Natl. Acad. Sci. USA* 84, 5038–5042.
18. Larochelle, A., Marceau, D., De Médicis, E.(1994) *J. Leukocyte Biol.* 55, 1.
19. Michalevicz, R., Revel, M. (1987) Interferons regulate the in vitro differentiation of multilineage lympho-myeloid stem cells in hairy cell leukemia. *Proc. Natl. Acad. Sci. USA* 84, 2307–2311.
20. De Braekeleer, M., St.-Pierre, C., Vigneault, A., Simard, H., de Médicis, E., (1991) Hemochromatosis and pyruvate kinase deficiency. Report of a case and review of literature. *Ann. Hematol.* 62, 188–189.
21. Zachée, P., Staal, G. E., Rijksen, G., De Bock, R., Couttenye, M. M., De Broe, M. E. (1989) Pyruvate kinase deficiency and delayed clinical response to recombinant human erythropietin treatment. *The Lancet* 1327–1328.
22. Vives-Corrons, J. L., Florense, L., Munconille, J., Nondedem, B., Rozman, C. (1979) *Acta Haemat* 61, 168.
23. Ohta, C., Katayama, N, Uno, N., Mirami, N., Karitoni, Y., Shirawaka, S. (1984) *Rinsho Ketsneki* 25, 75.
24. Ieki, R., Miwa, S., Fujii, H. Kudoh, S. Kimura, H., Takaku, F. (1990) *Am. J. Hematol.* 34, 64.
25. Rapaport, S. I. (1987) *Introduction of hematology.* 2nd Ed. J.B. Lippincott Co. Philadelphia, Chap. 14, pp 204–228.
26. de Maeyer-Guignard, J. (1996) Interferons alpha and beta. In *Les cytokines.* Ed. J. M. Cavaillon. Masson. Paris. Chap. 23. pp. 335–347.
27. Billiau, A., Dijkmans, R. (1990) Interferon gamma: mechanism of action and therapeutic potential. Biochem. Pharmacol., 40, 1433–1439.
28. Trinchieri, G., Perussia, B. (1985) Immune interferon: a pleiotropic lymphokine with multiples effects. Immunol. Today, 6, 131–136.

What is claimed is:

1. A composition that enhances lymphoblastic proliferation of a mixed leukocyte population, comprising a lymphoblastic proliferation enhancing amount of a hemolytic anemia-related factor (HMF) and red blood cells, in association with a carrier, wherein said HMF comprises the amino acid sequence as defined in SEQ ID NO:4.

2. The composition of claim 1, wherein said HMF is a fusion protein.

3. The composition of claim 2, wherein said fusion protein is a HMF-GST fusion.

4. A method for enhancing the lymphoblastic proliferation in a mixed leukocyte population, which comprises incubating said leukocyte population with lymphoblastic proliferation enhancing amount of hemolytic anemia related factor, HMF, comprising the amino acid sequence as defined in SEQ ID NO:4.

5. The method of claim 4, wherein red blood cells are incubated with said leukocyte population and said HMF and wherein said red blood cells further potentiate said lymphoblastic proliferation.

6. The method of claim 4, wherein said enhancement of lymphoblastic proliferation is observed after 3 days of incubation of said mixed leukocyte population with said HMF.

7. The method of claim 4, wherein said HMF is a fusion protein.

8. The method of claim 7, wherein said fusion protein is a HMF-GST fusion.

* * * * *